United States Patent [19]

Pasarela

[11] Patent Number: 4,529,436
[45] Date of Patent: Jul. 16, 1985

[54] COLD STABILIZATION OF AQUEOUS HERBICIDAL COMPOSITIONS WITH UREA

[75] Inventor: Nunzio R. Pasarela, Bridgewater, N.J.

[73] Assignee: American Cyanamid Company, Stamford, Conn.

[21] Appl. No.: 491,502

[22] Filed: May 4, 1983

Related U.S. Application Data

[63] Continuation-in-part of Ser. No. 373,927, May 3, 1982, abandoned.

[51] Int. Cl.$^3$ ............................................. A01N 43/56
[52] U.S. Cl. ...................................................... 71/92
[58] Field of Search ............................. 71/92, DIG. 1

[56] References Cited

U.S. PATENT DOCUMENTS

| | | | |
|---|---|---|---|
| 4,126,443 | 11/1978 | Gadea ....................................... | 71/92 |
| 4,163,662 | 8/1979 | Baker, Jr. ................................ | 71/120 |
| 4,289,525 | 9/1981 | Pasarela et al. ........................ | 71/92 |
| 4,369,057 | 1/1983 | Takeno et al. .......................... | 71/92 |
| 4,396,415 | 8/1983 | Synnatschke et al. ................. | 71/92 |

OTHER PUBLICATIONS

Cooper, "Freezing Point Depressant, etc.", CA83, No. 166504f, (1975).
Ueno et al., "Effects of Urea, etc.", CA63, pp. 5869–5870, (1965).
Grapp et al., "Frost Resistance, etc.", (1975), CA84, No. 110498k, (1976).
Anon., "Road Salt, Inhibitors, etc.", CA70, No. 70540v, (1969).

*Primary Examiner*—Richard L. Raymond
*Attorney, Agent, or Firm*—E. J. Tsevdos; A. R. Noë

[57] ABSTRACT

Aqueous herbicidal compositions containing urea and methods of preparations thereof. These compositions are characterized by increased resistance to precipitation of the toxicant at temperatures at or below the freezing point of water. When these solutions are returned to room temperature after being partially or completely frozen, stability of components is maintained.

5 Claims, No Drawings

COLD STABILIZATION OF AQUEOUS HERBICIDAL COMPOSITIONS WITH UREA

This application is a continuation-in-part of our co-pending application, Ser. No. 373,927, filed May 3, 1982 now abandoned.

The invention herein described relates to aqueous herbicidal compositions containing urea and the active herbicidal ingredient 1,2-dimethyl-3,5-diphenylpyrazolium methyl sulfate. At temperatures at or below freezing, the toxicant of these compositions resists precipitation. When solutions of the invention are partially or completely frozen and then returned to room temperature, stability of components is maintained.

By way of background, the herbicide 1,2-dimethyl-3,5-diphenylpyrazolium methyl sulfate, known as AVENGE ® herbicide, is represented by the following structural formula:

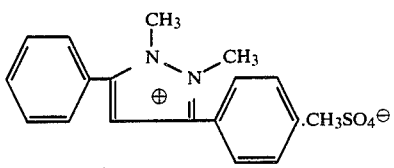

This compound is disclosed in U.S. Pat. No. 3,882,142 (1975), and has proven to be one of the most effective herbicides useful for the selective postemergence control of wild oats (*Avena fatua*) in the presence of small grains. The above herbicidal quaternary pyrazolium salt is highly soluble in water and allows easy preparation of aqueous concentrates. Such aqueous concentrates are quite convenient because of the ease with which they may be diluted prior to application.

Although concentrated aqueous solutions of AVENGE ® herbicide are quite stable at or above room temperature, they rapidly become unstable at temperatures at or below 0° C. (i.e., in winter storage) and tend to deposit copious amounts of crystalline 1,2-dimethyl-3,5-diphenylpyrazolium methyl sulfate. It has been found that once such deposits have formed at cold temperatures in herbicidal concentrates, they do not dissolve spontaneously when solutions are allowed to return to room temperature. Consequently, once partially crystallized, such formulations have to be heated and agitated until they enter solution and return to homogeneous form.

A method of preventing this cold-temperature-induced crystallization would make such concentrated herbicidal formulations considerably more desirable by facilitating their use.

In light of the foregoing summary of some demands and limitations of conventional herbicidal compositions containing 1,2-dimethyl-3,5-diphenylpyrazolium methyl sulfate, improved compositions resistant to cold-temperature-induced crystallization of the active toxicant, and methods of preparation thereof, are highly desirable. Accordingly, an object of this invention is to provide new and useful AVENGE ® herbicide compositions and methods for their preparation. This object is manifest in the appended claims.

It has been unexpectedly discovered that incorporation of urea into aqueous herbicidal formulations containing 1,2-dimethyl-3,5-diphenylpyrazolium methyl sulfate will permit these compositions to be frozen and upon subsequent thawing at room temperature to automatically reconstitute homogeneous solutions. More particularly, the invention herein described reveals the incorporation of urea in amounts ranging from about 5 to 20% by weight, and preferably from about 8 to 12% by weight, into aqueous herbicidal concentrates containing 1,2-dimethyl-3,5-diphenylpyrazolium methyl sulfate and a surfactant.

In the preparation of formulations of the invention the water component (preferably deionized for distilled and optionally heated to about 40° to 45° C.) is stirred and about 20% by weight (preferably 12 to 18%) of octylphenoxy polyethoxy ethanol is added. The mixture is stirred until a clear solution results. Then, about 20 to 46% by weight (preferably 28 to 35%) 1,2-dimethyl-3,5-diphenylpyrazolium methyl sulfate and about 5 to 20% by weight (preferably 8 to 12%) of urea are added and the mixture stirred until a homogeneous solution has formed. If desired, the resultant solutions may be clarified. Herbicidal solutions prepared in this manner may be cooled to the point of being partially or completely frozen, and when subsequently allowed to warm to room temperature form homogeneous solutions without the aid of additional heating and/or stirring.

The liquid non-ionic surfactant referred to above as octylphenoxy polyethoxy ethanol has an average molecular weight of 628 and contains an average of 9 to 10 ethylene oxide units, representing 67% by weight of the surfactant. The specific gravity of this surfactant is 1.065 at 25° C.; the viscosity is 240 cps at 25° C. (Brookfield; 12 r.p.m.), and the flash point is >148° C. (TOC). Alternatively, other similar nonionic surfactants can be substituted for octylphenoxy polyethoxy ethanol. For example, nonylphenoxy polyethoxy ethanol can be used. This compound has an average molecular weight of 640 and contains an average of 9 to 10 ethylene oxide units. The specific gravity of this surfactant is 1.056 at 25° C., the viscosity is 240 cps at 25° C. (Brookfield; 12 r.p.m.) and the flesh point is >148° C. (TOC).

Accordingly, a typical formulation may be prepared as follows: 1927.7 g water is heated to 40° C. and 505.5 g octylphenoxy polyethoxy ethanol is added with stirring. Stirring continues until a homogeneous solution forms. Next, 1348 g of 1,2-dimethyl-3,5-diphenylpyrazolium methyl sulfate (98% pure) and 328.8 g urea are added. The mixture is stirred until a clear solution forms. This solution may be chilled below the freezing point of water and then allowed to warm to room temperature to yield a homogeneous solution.

The invention is further illustrated but not limited by the examples set forth below.

EXAMPLE 1

General Preparation Procedure of aqueous herbicidal solutions for evaluation of storage stability at low temperatures Water (distilled or deionized) required to make the desired formulation is heated to about 40° to 45° C. The surfactant is added and the mixture is stirred until a homogeneous solution forms. Immediately thereafter 1,2-dimethyl-3,5-diphenylpyrazolium methyl sulfate and urea are added and the mixture is stirred until a homogeneous solution forms. The solution is cooled to room temperature and stored at −4° C. (25° F.) to determine the cold-temperature stability of the solution.

By the above-described procedure several formulations are prepared and evaluated. The composition of these formulations is given below.

| Component* | 1 | 2 | 3 | 4 |
|---|---|---|---|---|
| 1,2-dimethyl-3,5-diphenylpyrazolium methyl sulfate 99.2% pure | 32.8 | 32.8 | 32.8 | 32.8 |
| Octylphenoxy polyethoxy ethanol | 12.3 | 12.3 | 12.3 | 12.3 |
| Urea | 5.0 | 10.0 | — | 20.0 |
| Water | 49.9 | 44.9 | 54.9 | 34.9 |
| Total | 100.0 | 100.0 | 100.0 | 100.0 |

*Units are expressed on a gram weight basis

After storage at −4° C. (25° F.) for 5 days, Sample 3 is fully crystallized, Samples 1 and 2 show signs of crystallization and Sample 4 is free of crystals. Next, the samples are warmed to dissolve the crystals, seeded with crystals of 1,2-dimethyl-3,5-diphenylpyrazolium methyl sulfate, and again stored at −4° C. (25° F.). After one week's storage, all samples show the presence of significant amounts of crystals. On standing at room temperature, the crystals in Samples 2 and 4 dissolve in about one hours time without agitation or stirring. Crystals are present in Samples 1 and 3, even after 24 hours at room temperature.

EXAMPLE 2

Preparation aqueous herbicidal solutions for evaluation of storage stability at low temperatures By the procedure of Example 1, four large-scale samples are prepared and evaluated for storage stability at low temperatures. The composition of samples is given below.

EXAMPLE 2

| Component | 1 | | 2 | | 3 | | 4 | |
|---|---|---|---|---|---|---|---|---|
| | Weight (g) | % | Weight (g) | % | Weight (g) | % | Weight (g) | % |
| 1,2-dimethyl-3,5-diphenylpyrazolium methyl sulfate 98% pure | 1348.0 | 32.8 | 1348.0 | 32.8 | 1348.0 | 32.8 | 1348.0 | 32.8 |
| Octylphenoxy polyethoxy ethanol | 505.5 | 12.3 | 505.5 | 12.3 | 505.5 | 12.3 | 505.5 | 12.3 |
| Urea | | | 205.5 | 5.0 | 411.0 | 10.0 | 822.0 | 20.0 |
| Water | 2256.5 | 54.9 | 2051.0 | 49.9 | 1845.5 | 44.9 | 1434.5 | 34.9 |
| Total | 4110.0 | 100.0 | 4110.0 | 100.0 | 4110.0 | 100.0 | 4110.0 | 100.0 |

The above samples are stored at −4° C. (25° F.). After two-days storage, the solutions contain no crystals. The samples are then seeded with crystals of 1,2-dimethyl-3,5-diphenylpyrazolium methyl sulfate and returned to cold storage. One day after seeding, Samples 1 and 4 are frozen solid, Sample 2 is a mixture of ice and herbicide crystals, while Sample 3 is approximately 50% ice and 50% solution. Four days after seeding and storage at −4° C. (25° F.) Samples 1 and 4 are solids containing some crystals, while Samples 2 and 3 are mixtures of ice and liquid. Additional storage for a week at the above temperature produces no further visible changes. The samples are then removed from cold storage and allowed to warm slowly. After two hours, the temperature of the samples rises to −2° C., Sample 3 is about 75% solid and Sample 2 is about 25% solid. After about four hours the temperature of the samples rises to 3° C. Sample 2 is completely in solution, Sample 3 is about 50% dissolved, and Samples 1 and 4 are less than 50% in solution. One day later all four samples are liquid but Samples 1 and 4 contains crystals of 1,2-dimethyl-3,5-diphenylpyrazolium methyl sulfate.

EXAMPLE 3

Preparation of aqueous herbicidal solutions for evaluation of low-temperature storage stability By the procedure of Example 1, three large-scale samples are prepared and evaluated for storage stability at low temperatures. The composition of the samples is given below.

EXAMPLE 3

| Component | 1 | | 2 | | 3 | |
|---|---|---|---|---|---|---|
| | Weight (g) | % | Weight (g) | % | Weight (g) | % |
| 1,2-dimethyl-3,5-diphenyl pyrazolium methyl sulfate 98% pure | 1348.0 | 32.80 | 1348.0 | 32.80 | 1120.0 | 28.00 |
| Octylphenoxy polyethoxy ethanol | 505.5 | 12.30 | 505.5 | 12.30 | 600.0 | 15.00 |
| Urea | 328.8 | 8.00 | 493.2 | 12.00 | 320.0 | 8.00 |
| Water | 1927.7 | 46.90 | 1763.3 | 42.90 | 1960.0 | 49.00 |
| Total | 4110.0 | 100.00 | 4110.0 | 100.00 | 4000.0 | 100.00 |

All of the above solutions are cold-stored during this experiment at −8° C. (17.6° F.). After two days of storage, Samples 1 and 2 are still mostly liquid and Sample 3 is about ⅔ ice + ⅓ liquid. After an additional three days of storage, Samples 1 and 3 are about ⅔ ice + ⅓ liquid while Sample 2 is about ⅓ ice + ⅔ liquids. After three more days of storage no further changes are noted in Samples 1 and 3, but Sample 2 is now about ⅔ ice + ⅓ liquid. When stored at room temperature, all three samples become homogeneous liquids within 24 hours.

EXAMPLE 4

Preparation of various formulations of aqueous herbicidal solutions for stability tests at low temperatures By the method of Example 1, eight samples are prepared and evaluated for storage stability at low temperatures. The composition of the samples is given below.

EXAMPLE 4

| | 1 | 2 | 3 | 4 |
|---|---|---|---|---|
| | Weight | Weight | Weight | Weight |

EXAMPLE 4-continued

| Component | (g) | % | (g) | % | (g) | % | (g) | % |
|---|---|---|---|---|---|---|---|---|
| 1,2-dimethyl-3,5-diphenylpyrazolium methyl sulfate 98% | 164.0 | 32.8 | 164.0 | 32.8 | 164.0 | 32.8 | 164.0 | 32.8 |
| Octylphenoxy polyethoxy ethanol | 61.5 | 12.3 | 61.5 | 12.3 | 61.5 | 12.3 | 61.5 | 12.3 |
| Urea | 30.0 | 6.0 | 70.0 | 14.0 | 80.0 | 16.0 | 90.0 | 18.0 |
| Water | 244.5 | 48.9 | 204.5 | 40.9 | 194.5 | 38.9 | 184.5 | 36.9 |
| Total | 500.0 | 100.0 | 500.0 | 100.0 | 500.0 | 100.0 | 500.0 | 100.0 |

| | 5 | | 6 | | 7 | | 8 | |
|---|---|---|---|---|---|---|---|---|
| Component | Weight (g) | % | Weight (g) | % | Weight (g) | % | Weight (g) | % |
| 1,2-dimethyl-3,5-diphenylpyrazolium methyl sulfate 98% pure | 1890.6 | 46.0 | 140.0 | 28.0 | 174.2 | 34.84 | 207.95 | 41.59 |
| Octylphenoxy polyethoxy ethanol | 727.5 | 17.7 | 75.0 | 15.0 | 93.75 | 18.75 | 111.90 | 22.38 |
| Urea | 345.3 | 8.4 | 25.6 | 5.12 | 31.85 | 6.37 | 38.00 | 7.60 |
| Water | 1146.6 | 27.9 | 259.4 | 51.88 | 200.2 | 40.04 | 142.15 | 28.43 |
| Total | 4110.0 | 100.0 | 500.0 | 100.0 | 500.0 | 100.0 | 500.0 | 100.0 |

All samples are stored at −4° C. (25° F.) for 24 hours. Examination shows that under these conditions, all remained clear liquids and no crystals formed. The samples are seeded with crystals of 1,2-dimethyl-3,5-diphenylpyrazolium methyl sulfate and placed in cold storage at −9° C. (15° F.). Four days later, Samples 1, 3, 4, 5, 6, and 8 are completely solidified. Sample 2 remains a liquid and Sample 7 is about 85% liquid and 15% solid. After four hours at room temperature, Samples 1, 6, and 7 are liquids, each containing a small amount (>2%) of crystals; Samples 2 and 3 are clear solutions, while Samples 4, 5, 7 and 8 contain an appreciable amount of crystals. The samples are allowed to warm to 19°–20° C. and are then reexamined. Sample 1 contains approximately 1% crystals. Samples 3, 6 and 7 each contain a trace amount of solids while Samples 4 and 5 contain about 5% solids. When these samples are shaken, clear solutions form. Sample 8 contains about 15 to 20% solids while Sample 2 is a clear liquid.

EXAMPLE 5

Evaluation of the cold stroage stability of herbicidal solutions with and without supplements of urea By the method of Example 1, the following formulations are prepared. Each contains 200 g/liter of 1,2-dimethyl-3,5-diphenylpyrazolium cation. The compositions are given below.

EXAMPLE 5

| | 1 | | 2 | |
|---|---|---|---|---|
| Component | Weight (g) | % | Weight (g) | % |
| 1,2-dimethyl-3,5-diphenylpyrazolium methyl sulfate 98% pure | 1120.0 | 28.00 | 1120.0 | 28.00 |
| Octylphenoxy polyethoxy ethanol | 600.0 | 15.00 | 600.0 | 15.00 |
| Urea | — | — | 320.0 | 8.00 |
| Water | 2280.0 | 57.00 | 1960.0 | 49.00 |
| Total | 4000.0 | 100.0 | 4000.0 | 100.0 |

Samples of both formulations are stored in one-gallon translucent plastic jugs for a period of three weeks in a storage building where they are exposed to temperatures of from −20° C. to 0° C. for the storage period. At the end of the storage period, the jug containing formula (I) (not urea present) is frozen solid; whereas, the jug containing formula II (8% urea present) contains a slush. The jugs are then placed in a warm storage space (22° C.) for two days. On examination of the jugs after two days in warm storage, it is found that the jug containing formula I (no urea present) has a two to three centimeter layer of white, 1,2-dimethyl-3,5-diphenylpyrazolium methyl sulfate, crystals at the bottom of the jug; whereas, the jug containing formula II is a uniform liquid with no observable 1,2-dimethyl-3,5-diphenylpyrazolium methyl sulfate crystals deposited at the bottom of the jug.

The above procedure is repeated using another set of one-gallon jugs, one containing formula I and the other containing formula II, excepting that the jugs are placed in cold storage at −40° C. to 7° C. for three weeks and then removed and examined. The jug containing formula I is frozen solid and has a two to three centimeter layer of white, 1,2-dimethyl-3,5-diphenylpyrazolium methyl sulfate, crystals covering the bottom of the jug; whereas, the jug containing formula II has some ice crystals in the top third of the jug and only a dusting (0.5 cm) of white, 1,2-dimethyl-3,5-diphenylpyrazolium methyl sulfate, crystals on the bottom of the jug.

The jugs are then placed in warm storage (22° C.) for two days and again examined. Examination shows that the jig containing formula II (8% urea present) is a uniform solution with no observable sedimentation; whereas, the jug containing formula I (no urea present) has a two to three centimeter layer of white crystals remaining on the bottom.

These data clearly demonstrate the low temperature stability, i.e., −20° C. to −40° C., of the formula II composition of the invention which contains 8% by weight of urea and the low temperature instability of the formula I composition which contains no urea.

In practice, it has been found that when 1,2-dimethyl-3,5-diphenylpyrazolium methyl sulfate is precipitated from an aqueous formulation containing only 1,2-dimethyl-3,5-diphenylpyrazolium methyl sulfate, water, and a surfactant, the precipitate is extremely difficult to dislodge and redissolve.

What is claimed is:

1. An aqueous herbicidal composition, comprising, on a weight basis: about 20% to 46% 1,2-dimethyl-3,5-diphenylpyrazolium methyl sulfate, 10% to 20% octylphenoxy polyethoxy ethanol, 5% to 18% urea, and water sufficient to total said composition to 100%; wherein when said composition is cooled to the point of being partially or completely frozen and subsequently allowed to warm to room temperature, said composition forms homogeneous solution without the aid of additional heating or stirring.

2. A composition according to claim 1, wherein 32.8% of the formulation is 1,2-dimethyl-3,5-diphenylpyrazolium methyl sulfate; 12.3% is octylphenoxy polyethioxy ethanol; 8% is urea, and 46.9% is water.

3. A composition according to claim 1, wherein 28.0% of said formulation is 1,2-dimethyl-3,5-diphenylpyrazolium methyl sulfate; 15.0% is octylphenoxy polyethoxy ethanol; 8.0% is urea, and 49.0% is water.

4. A composition according to claim 1, wherein 46.0% is 1,2-dimethyl-3,5-diphenylpyrazolium methyl sulfate; 17.7% is octylphenoxy polyethoxy ethanol; 8.4% is urea, and 27.9% is water.

5. A composition according to claim 1, wherein 41.59% is 1,2-dimethyl-3,5-diphenylpyrazolium methyl sulfate; 22.38% is octylphenoxy polyethoxy ethanol; 7.6% is urea, and 28.43% is water.

* * * * *